United States Patent [19]
Hille et al.

[11] Patent Number: 5,990,229
[45] Date of Patent: Nov. 23, 1999

[54] ADHESIVES WITH LOW LEVEL OF RESIDUAL MONOMERS AND PROCESS FOR MANUFACTURING SAME

[75] Inventors: Thomas Hille, Neuwied, Germany; Paul M. Petersen, Princeton, N.J.; James Burkert, Rahway, N.J.; Paul B. Foreman, Somerville, N.J.

[73] Assignee: National Starch and Chemical Investment Holding Corporation, Wilmington, Del.

[21] Appl. No.: 08/928,313

[22] Filed: Sep. 12, 1997

[51] Int. Cl.$^6$ .................................. C08F 2/06; C08F 8/42
[52] U.S. Cl. ......................... 524/556; 524/555; 525/370; 528/481; 528/485; 528/495; 528/499; 528/500; 528/501
[58] Field of Search ...................... 524/555, 556; 528/481, 485, 495, 499, 500, 501; 525/370, 339

[56] References Cited

U.S. PATENT DOCUMENTS

| | | | |
|---|---|---|---|
| 3,023,201 | 2/1962 | Moberly et al. | 260/94.7 |
| 3,331,824 | 7/1967 | Folzenlogen et al. | 260/88.2 |
| 3,632,740 | 1/1972 | Robinson et al. | 424/28 |
| 3,769,071 | 10/1973 | Trancik | 117/122 P |
| 3,896,789 | 7/1975 | Trancik | 128/2 R |
| 4,273,722 | 6/1981 | Koritala | 260/409 |
| 4,375,529 | 3/1983 | Fong et al. | 524/555 |
| 4,560,553 | 12/1985 | Zupan | 424/78 |
| 4,655,768 | 4/1987 | Marecki et al. | 604/897 |
| 4,883,669 | 11/1989 | Chien et al. | 424/448 |
| 4,906,169 | 3/1990 | Chien et al. | 424/448 |
| 4,929,717 | 5/1990 | Chmelir | 528/490 |
| 5,478,922 | 12/1995 | Rhee et al. | 528/483 |
| 5,705,571 | 1/1998 | Tsiang et al. | 525/339 |

FOREIGN PATENT DOCUMENTS

| | | | |
|---|---|---|---|
| 880595 | 12/1979 | Belgium . | |
| 0 209 956 A1 | 1/1987 | European Pat. Off. | C08G 61/02 |
| 0 363 795 A2 | 4/1990 | European Pat. Off. | C08F 4/40 |
| 0 521 620 A1 | 1/1993 | European Pat. Off. | C08F 6/00 |
| 0 544 325 A1 | 6/1993 | European Pat. Off. | C08F 8/04 |
| 0 696 603 A1 | 2/1996 | European Pat. Off. | C08F 297/04 |
| 0 725 087 A1 | 8/1996 | European Pat. Off. | C08F 8/04 |
| 43 03 616 C1 | 8/1994 | Germany | C09J 133/08 |

OTHER PUBLICATIONS

"General Characteristics of Surfactants", ICI Americas Inc., Wilmington, Delaware 19897, Oct. 1979.

Takashiro Muroi, "Catalysts and Processes for the Hydrogenation of Polymers", *CCN Chemical Catalyst News*, Issued by Engelhard Corporation, Sep. 1993.

*Primary Examiner*—James J. Seidleck
*Assistant Examiner*—Olga Asinovsky
*Attorney, Agent, or Firm*—Lydia T. McNally; Jane E. Gennaro

[57] ABSTRACT

An adhesive, which contains olefinic polymers and less than 1% by weight of free monomers, is manufactured via catalytic hydrogenation. It is preferably used in the area of cosmetics, in the foods sector, in medicinal plasters and transdermal systems.

10 Claims, No Drawings

ADHESIVES WITH LOW LEVEL OF RESIDUAL MONOMERS AND PROCESS FOR MANUFACTURING SAME

FIELD OF THE INVENTION

This invention relates to adhesives containing polymers with a very low content of residual monomers, a process for their manufacture, and their application.

BACKGROUND OF THE INVENTION

Typically speaking, adhesive tapes, sticking plasters and the like are manufactured by coating films or paper with polymer solutions or suspensions. Subsequently, the organic solvents or the water are removed by drying. Especially suitable are solutions of polyacrylates in organic solvents. These polyacrylate solutions are normally manufactured by polymerizing acrylic acid, its ester and, in some cases, vinyl acetate, while adding free-radical initiators, e.g. azobisisobutyronitrile or others. After the completion of polymerization or copolymerization, organic solvents are added to dilute to a solids content of approximately 40%, after which the solution is ready for coating.

In the recent past it has been recognized that this process has a limitation, especially in cases of copolymerization, which is that the least reactive monomer escapes polymerization. For this reason, in order to arrive at a defined polymer on a reproducible basis, an excess of this least reactive monomer, e.g. vinyl acetate, is used. In principle, vinyl acetate is slower to react than the acrylates as the double bond it contains is not conjugated with a carbonyl group. The disadvantage of adding an excess of vinyl acetate is that the proportion of free vinyl acetate in the solution can amount to up to 7–8% in relation to the solids content. Because of the dilution already referred to above, this residual monomer content can be reduced to approximately 3%.

In general, residual monomer contents of this order of magnitude are undesirable in adhesives, particularly for applications in the medical and cosmetics fields and for packaging in the foods sector. In addition, maximum residual monomer concentrations are prescribed by law in many countries. Therefore, there has been an industry-wide campaign aimed a reducing the content of residual polymers in polymer solutions for the medical and foods sector.

One attempted method is known as stripping distillation. In this, the solvents which originate from the synthesis of polymers are removed almost completely. Since the physical properties of vinyl acetate and ethyl acetate (boiling point, vapor pressure) differ only little, it is necessary either to evaporate to dryness or to constantly supplement the distilled ethyl acetate. Evaporating to dryness may lead to such a high temperature load that the polymer may change. Supplementing the ethyl acetate that has been distilled off leads to a high solvent consumption and to large quantities of solvent waste, an extremely expensive process.

Another method for removing residual monomers is to react the unconverted residual monomers with extremely reactive radical initiators based on organic peroxides, which are known as scavengers. The drawback of this process is that the residual monomers are not removed but react to form oligomers that remain in the polymer.

A desirable process, therefore, should have the following advantages: it should produce a polymer with an extremely low proportion of non-converted monomers or oligomers; the thermal load during polymerization or during the removal of the solvent should be minimized; it should use only small quantities of organic solvents; it should avoid the use of scavengers; and it should be economical.

SUMMARY OF THE INVENTION

It has now been discovered that polymer adhesives having a very low residual monomer content can be manufactured by means of catalytic hydrogenation and achieve the above mentioned advantages.

The resulting adhesives comprise polymers prepared from olefinic monomers and contain a very low content of residual monomers. These adhesives are suitable for use in technical applications, e.g. in adhesive tapes as office materials, or for cosmetic or medicinal applications, e.g. for the manufacture of sticking plasters, electrode plasters, or transdermal therapeutic systems.

Thus, this invention is an adhesive comprising one or more polymers prepared from olefinic monomers, wherein the content of free residual monomers is less than 1% by weight, preferably is less than 0.3% by weight, more preferably is less than 0.02% by weight, and most preferably is less than 0.01% by weight, but not less than 0.0001% by weight.

The polymers can be a homopolymer or a mixture of different homopolymers; a copolymer or a mixture of different copolymers; a block polymer or a mixture of different block polymers; or can be a mixture of one or more homopolymers, copolymers, or block polymers. The adhesives according to the invention may contain further substances, such as adhesive resins, e.g. hydrogenated colophonium; however, they may also consist entirely of the said polymers.

The invention relates specifically to pressure-sensitive adhesives, especially those that contain one or more copolymers from monomers such as acrylic acid, methacrylic acid, and acrylate and methacrylate esters, in which the ester part can contain up to 8 carbon atoms ($C_1$ –$C_8$ alkyl), or that contain copolymers of the above-mentioned monomers and the monomers vinyl acetate or styrene. Suitable acrylate and methacrylate esters are methyl, ethyl, straight-chain or branched propyl, butyl, pentyl, hexyl, heptyl or octyl esters, e.g. ethylhexyl ester, or hydroxy esters, e.g. hydroxyethyl ester.

The invention relates especially to pressure-sensitive adhesives that contain a copolymer of 2-ethylhexyl acrylate and vinyl acetate.

In another embodiment this invention is a process for the manufacture of an adhesive comprising one or more olefinic polymers, wherein the content of free monomers is less than 1% by wright, the process comprising, after completion of polymerization or copolymerization of the polymer, the hydrogenation of the adhesive in an organic solvent in the presence of a heterogeneous or homogeneous catalyst.

Any suitable catalyst, such as platinum, palladium, and palladium on activated carbon can be used. Suitable heterogeneous catalysts are palladium on activated carbon and nickel on silica/alumina. A suitable homogeneous catalyst is tris(triphenylphosphine) rhodium (I) chloride.

The hydrogenation process will take place at temperatures of up to 150° C. and at hydrogen pressures of up to 100 bar, preferably at temperatures of up to 100° C. and at hydrogen pressures of up to 80 bar, more preferably at temperatures of up to 100° C. and at hydrogen pressures of up to 52 bar, and most preferably at room temperature and at atmospheric pressure.

The hydrogenation may be accomplished in any suitable organic solvent, and particularly in an organic solvent less polar than water. A preferable solvent is ethyl acetate.

These adhesives are useful wherever there is a need for materials with low residual monomer content, such as, for example, in transdermal therapeutic systems and bandages, including transdermal systems that may have cosmetic utility, and also as packaging adhesives for food products. These adhesives may also be utilized in medicinal plasters, which for purposes herein includes veterinary medicinal plasters.

Particularly, this invention also relates to transdermal therapeutic systems that contain an adhesive in accordance with the invention, especially a pressure-sensitive adhesive, e.g. a copolymer of 2-ethylhexyl acrylate and vinyl acetate. Such transdermal therapeutic systems typically consist of a reservoir, which contains the active agent to be delivered, and an adjacent layer made of a pressure-sensitive adhesive which is brought into contact with the skin.

In such a system, however, the pressure-sensitive adhesive can also form a single-layer or multi-layer matrix which is brought into contact with the skin and in which the active agent is present in a dispersed or even in a dissolved form. If the matrix is multi-layered, the individual layers can consist of different adhesives in accordance with the invention.

DETAILED DESCRIPTION OF THE INVENTION

The catalytic hydrogenation of C=C double bonds in alkenes in the presence of platinum or palladium or palladium on carbon (Pd/C) or other metals of the 8th auxiliary group of the periodic system (e.g. nickel) as a catalyst at atmospheric or increased hydrogen pressure and at room temperature or at higher temperatures has in itself long been known. However, it was not expected that the present problem could be solved by applying the well-known hydrogenation process, since the process has to be conducted under the most unfavorable conditions.

Prior to hydrogenation, for example, the concentration of residual monomers is very low (<3%). Moreover, as will be known, hydrogenation with metallic catalysts takes place more unfavorably according as the solvent used is more non-polar. As the hydrogenation following the polymerization takes place in the present case in what are essentially non-polar organic solvents, e.g. in ethyl acetate, this implies a further unfavorable reaction condition. Nevertheless, through the use of the process according to the invention, the content of residual monomers can be successfully reduced to below 0.3%, and even as low as 0.01%.

The fact that this is not a foregone conclusion is demonstrated by the U.S. Pat. No. 4,375,529 (Fong et al.). That patent describes a method for reducing the content of residual monomers in a water-oil emulsion containing partially polymerized acrylamide and sodium acrylate. The degree of polymerisation described in that patent specification amounted to only 80%, which implies that the concentration of residual monomers amounted to approx. 20%.

The subsequent hydrogenation took place in water, which is a highly polar solvent. At the same time it was possible to use very high pressures. None the less, the residual monomer concentrations that were achieved were around 1% at best and, for the reasons outlined above, these are unacceptably high and could likewise be achieved by means of suitable polymerisation techniques.

The process according to the invention is carried out through hydrogenation of a solution of the adhesive in organic solvents in the presence of a metallic catalyst at temperatures of up to 150° C., preferably up to 100° C. and in a pressure range from 0.3 bar up to 100 bar, preferably from 0.5 bar up to 80 bar.

A particularly preferred process is hydrogenation in the presence of platinum, palladium or palladium on carbon at room temperature and atmospheric hydrogen pressure. The process according to the invention can also be carried out in the presence of other metals of the 8th auxiliary group of the periodic system, e.g. using nickel as a catalyst, at higher temperatures and at a higher hydrogen pressure.

The preferred solvents are those which are less polar than water (i.e. those whose dielectric constant is lower than that of water). An especially preferred solvent is ethyl acetate.

It will be recognized that in transdermal therapeutic systems any unreacted monomer or by-product of polymerization initiators that are present in the adhesive and that are potentially able to react with the drug to be delivered in the transdermal system are undesirable. Therefore, it is a distinct advantage to be able to reduce the level of residual monomers or other reactive compounds to as low a level as possible for adhesives that will be used in such therapeutic systems.

Further, utilizing a hydrogenation technique to reduce the level of vinyl acetate produces ethyl acetate as the product. Since ethyl acetate is often the solvent of choice for the adhesive, no new component is added to the adhesive matrix.

The following Examples will serve to further describe the invention, but are not deemed a limitation. Descriptions of the hydrogenation and detection procedures used in the Examples are disclosed in the Procedures section following the Examples.

EXAMPLES

Example 1. Hydrogenation of vinyl acetate formulation. A copolymer prepared from vinyl acetate, 2-hydroxyethyl acrylate (2-HEA), 2-ethylhexylacrylate (2-EHA), and gylcidyl methacrylate (GMA) was formulated to 10% solids in ethyl acetate, hydrogenated under conditions as disclosed in Table 1 using the catalyst at 10% by weight of the polymer solution, and then evaluated for residual vinyl acetate monomer (VAM). The data show that the reduction of residual vinyl acetate occurs, even under mild conditions of room temperature and one atmosphere of hydrogen, using a palladium on activated carbon catalyst. The data also show that the supported nickel catalyst, although ineffective under mild conditions, is effective at the more vigorous conditions of 80° C. and 52 bar hydrogen. The experiment using no hydrogen was performed to demonstrate that in fact reduction was taking place and not just absorption of the vinyl acetate onto the carbon of the catalyst. Although idealized conditions were used, the 10% polymer solids and 10% loading of catalyst, these experiments show that the level of residual vinyl acetate monomer can be reduced by catalytic reduction using either a palladium or nickel based catalyst where conditions are optimized for the particular catalyst. The preferred catalyst is the palladium catalyst.

TABLE 1

Effect of hydrogenation on VAM

| Catalyst 10% by wt of polymer solution | Hydrogenation Conditions | VAM in ppm[e] unreduced | VAM in ppm[e] reduced |
|---|---|---|---|
| 5% Pd/C[a] | RT/1 atm H2[d] 16 hours | 17,700 | <220 |
| 55% Ni/Si[b] | RT/1 atm H2 16 hours | 17,700 | 16,500 |
| 5% Pd/C | RT/no H2 16 hours | 17,700 | 16,500 |
| 55% Ni/Si | 50° C./52 bar H2 14 hours | 36,000 | 40,000 |
| 65% Ni/Si/Al[c] | 50° C./52 bar H2 14 hours | 42,000 | 16,000 |
| 65% Ni/Si/Al | 80° C./52 bar H2 14 hours | 34,700 | 350 |

Notes:
[a]palladium on activated carbon
[b]nickel on silica
[c]nickel on silica/alumina
[d]room temperature and 1 atmosphere hydrogen
[e]based on 100% polymer solids Example 2. Effect of hydrogenation using higher polymer solids. The experiments in this example were conducted to determine whether reduction could be obtained on higher solids materials than 10%. The hydrogenation was carried out on the same copolymer as used in Example 1 under hydrogenation conditions of 80° C. and 52 bar hydrogen pressure, using either a 5% palladium on activated carbon catalyst or 65% nickel on silica/alumina catalyst, with the catalyst loaded at 10% by weight of the polymer solution. The results are set out in Table 2a and indicate that the level of residual VAM can be reduced below the 1000 ppm level when the reaction is performed at any concentration at least up to about 50% solids.

TABLE 2a

Variation in Polymer Solids

| Catalyst at 10% by weight of polymer solution | % Polymer Solids | VAM unreduced ppma | VAM reduced ppma |
|---|---|---|---|
| Pd/C RT/1 atm H2 16 hours | 10 | 16,500 | <220 |
|  | 25 | 17,900 | <200 |
|  | 50 | 18,700 | <110 |
| 65% Ni/Si/Al 80° C./52 bar H2 16 hours | 10 | 34,700 | 350 |
|  | 50 | 33,800 | <110 |

Notes:
a. based on 100% polymer solids

This is important because the viscosity of the matrix greatly increases with the percent solids of the formulation as shown in Table 2b. Thus the data in Table 2a further illustrate that the hydrogenation is effective in a very viscous matrix.

TABLE 2b

Viscosity Table

| Solids/% | Viscosity/cp |
|---|---|
| 51.5 | 22500 |
| 40 | 2700 |
| 35 | 1240 |
| 30 | 580 |
| 25 | 290 |

Example 3. Effect of hydrogenation on other residual monomers. The same copolymer as used in Example 1 was tested for the presence of the monomers other than vinyl acetate after the hydrogenation. The only monomer present at a detectable level was 2-EHA; residual 2-HEA and GMA may have been present, but were below detectable limits. The results are set out in Table 3, and show that when residual vinyl acetate is reduced using the disclosed hydrogenation conditions, so too are residual acrylates.

TABLE 3

Effect of hydrogenation on 2-HEA

| Hydrogenation Conditions | unreduced 2-HEA | reduced 2-EHA |
|---|---|---|
| 50% polymer solids, 5% Pd/C at 10% by wt of polymer solution, RT, 1 atm H2, 16 hours | 48 ppm | <20 ppm |
| 10% polymer solids 65% Ni/Si/Al at 10% by wt of polymer solution, 80° C., 52 bar H2, 16 hours | 44 ppm | <5 ppm |

Example 4. Hydrogenation of all acrylate formulation. An all acrylate copolymer was prepared from 2-ethylhexyl acrylate (2-EHA), methyl acrylate, acrylic acid, and glycicyl methacrylate, and formulated to 37% polymer solids in a solvent mixture of 54% ethyl acetate, 34.6% isopropanol, and 11.4% hexane. The polymer solution was subjected to hydrogenation conditions of 80° C. and 52 bar hydrogen pressure using a 65% nickel on silica/alumina catalyst. The results are reported here in Table 4 and show that using the hydrogenation conditions disclosed, the level of residual acrylate monomers can be effectively reduced.

TABLE 4

| Sample | Monomer Concentration in ppm | | | |
|---|---|---|---|---|
|  | 2-ethylhexyl acrylate | methyl acrylate | acrylic acid | glycidyl methacrylate |
| unreduced | 7,360 | <200 | 920 | <200 |
| reduced | <75 | <200 | 50 | <200 |

Example 5. Level of catalyst employed and residual catalyst. It is advantageous to keep the level of catalyst as low as possible for reasons of economy and to make the removal of the catalyst easier.

(a) In this example, the hydrogenation was performed using 5% Pd on activated carbon at a catalyst loading level down to 0.05% and 0.1% by weight of polymer solution. The copolymer composition was that used in Example 1 and the polymer solution had a 50% solids content. The hydrogenation conditions and residual vinyl acetate monomer levels before and after the hydrogenation are reported in Table 5. The results indicate that the hydrogenation was effective even at a catalyst loading level of 0.05%.

In order to test for residual Pd content, the reduced polymer solution was filtered to remove the catalyst, and the residual Pd level determined by atomic absorption testing. The filtration was conducted utilizing 3.0 μm Millipore filter paper at 4 bar and 60° C. All four of the samples in Table 5 showed low levels of Pd (<2 ppm). One of the samples was left to stand for two weeks, and after that time was filtered and analyzed for Pd content. This sample showed no significant increase in Pd content from that filtered directly after hydrogenation. All four samples exhibited unchanged color after hydrogenation from the polymer color before hydrogenation. The results are reported here in Table 5.

TABLE 5

Level of 5% Pd/C Catalyst

| Catalyst level by % polymer solution | Hydrogenation Conditions 60° C., 52 bar H2 | Residual VAM ppm | | Residual Pd in ppm after filtration |
|---|---|---|---|---|
| | | unreduced | reduced | |
| 0.1 | 1 hour | 16,000 | <50 | <0.1 |
| 0.1 | 1 hour | 16,000 | <50 | 1.5 |
| 0.05 | 3 hours | 16,000 | <50 | 0.4 |
| 0.1 | 1 hour | 16,000 | <50 | 1.1 filtered after 2 weeks storage |

Additional filtrations were conducted using a 5 μm and a 1.0 μm Millipore filter paper. The 5.0 μm paper was ineffective in removing the catalyst, but coating the paper with a Celite pad improved the filtration. The 1.0 μm paper did not allow passage of the polymer solution or catalyst at 60° C. and up to 8 bar nitrogen pressure. To test for effective filtration on an industrial scale-up, commercial filter paper at 60° C. and 7 bar was used to conduct a filtration on the same sample and found to be effective to remove the catalyst.

(b) Residual Ni catalyst. A polymer sample at 50% solids was hydrogenated under 52 bar hydrogen pressure and 80° C. using a 65% nickel catalyst on silica/alumina with a catalyst loading of 10% by weight of polymer solution. The residual VAM in this sample was 55 ppm based on 50% solids, and the nickel content, based on the 50% solids in ethyl acetate was 5.1 ppm.

Example 6. Hydrogenation with Large Particle Size Catalyst. In the previous examples, the catalyst was used in powdered form, and although the reduction worked very well, the filtering of this powder from the polymer solution at the end of the hydrogenation added an extra step to the process. To avoid the necessity of filtering, in this example large particle size catalysts were used in the hydrogenation reaction. The catalysts, in pellet or chip form, were suspended in a wire mesh basket in the reactor and the mixing blades of the reactor positioned to direct the flow of the polymer solution through the basket. This use of large particle size catalysts simulates the type of system used in, for example, a commercial fixed bed continuous hydrogenation apparatus.

Two different catalysts were used: a 0.50% palladium on alumina 3.2 mm pellet, and a 1.0% palladium on carbon 4×8 mesh chip. All reactions were performed at 48 bar hydrogen pressure and at the temperatures and for the times reported in Table 6 on polymer solutions at 50% polymer solids. The same copolymer as used in Example 1 was employed. As can be seen from the data, hydrogenation can be effected using large particle size catalysts.

TABLE 6

| Conditions | | Catalyst | | VAM* content in ppm | |
|---|---|---|---|---|---|
| Hours | °C. | Composition | Form | unreduced | reduced |
| 70 | 35–45 | 0.5% Pd/Al | pellet 3.2 mm | 2700 | <10 |
| 4 | 35–45 | 0.5% Pd/Al | pellet 3.2 mm | 2700 | 25 |
| 2 | 35–45 | 0.5% Pd/Al | pellet 3.2 mm | 3150 | 1340 |
| 2 | 50 | 1.0% Pd/C | 4 × 8 mesh | 3400 | <24 |

*All monomer concentrations are of a 10% solids solution. The monomer concentration based on 100% solids would be greater by a factor of 10.

Example 7. Hydrogenation with Homogeneous Catalyst. When heterogeneous catalysts are used in the hydrogenation process, as was done in the previous examples, the catalyst generally is removed by filtration at the completion of the hydrogenation. When a homogeneous catalyst is used, the filtration step can be avoided inasmuch as the catalyst can be left in solution because it is used in such a minor amount. This makes a more efficient process. In this example a homogeneous catalyst was used to hydrogenate the polymer solution in Example 1, containing about 16000 ppm of residual vinyl acetate. Various homogeneous catalysts are known and used in the art for hydrogenation, and can be utilized for the hydrogenation process disclosed in this specification.

The specific catalyst used in this example was Wilkinson's catalyst, tris(triphenylphosphine) rhodium (I) chloride, and was used in an amount of 1 ppm (about 0.1 ppm rhodium), based on total sample weight. The hydrogenation was conducted at 60° C. for 16 hours using 48 bar hydrogen. At this level the residual vinyl acetate monomer remained the same. The hydrogenation was repeated employing 10 ppm of Wilkinson's catalyst (about 1 ppm rhodium) at 60° C. and 16 hours using 48 bar hydrogen. In this second experiment, the residual VAM was reduced from 16200 ppm to 2900 ppm.

Example 8. Hydrogenation of residual initiators. In order to test the effectiveness of the hydrogenation on residual polymer initiators that would be present in the polymer solution, a sample of a pressure sensitive polymer that contained 250 ppm of residual benzoyl peroxide was subjected to the hydrogenation conditions of 5% palladium on activated carbon at a 0.05 weight percent loading of the catalyst per polymer solids, 60° C., and 48 bar hydrogen pressure for 16 hours. Analysis of the sample after the hydrogenation disclosed no detectable benzoyl peroxide.

Procedures

Method of Detection for Residuals.

Each formulation was tested both before and after hydrogenation for residual monomer or by-product content by direct injection gas chromatography with a Hewlett-Packard 5890 GC/FID using an external standard. The chromatographic conditions for the tests were: GC column: 30 m ×0.53 mm I.D. DB-624 (3 μm film) or equivalent Oven: 45° C. for 5 min; 30° C/min to 230° C. Injector: 180° C. Detector: 275° C. Carrier gas: 8 ml/min Helium.

Hydrogenation Employing Heterogeneous Catalysis

A sample of the copolymer of Example 1, 1000 g at ~50% solids in ethyl acetate, was poured into a 2000 ml Parr Pressure Reactor and 0.5 g of palladium on activated carbon (5% Pd) powdered catalyst was added. The reactor was sealed, then purged twice with 14 bar of nitrogen gas, and twice with 35 bar hydrogen gas. The reactor was pressurized with 48 bar of hydrogen gas and heated to 60° C., which raised the pressure to ~52 bar. The reaction mixture was then stirred at 1000 RPM for 1 hour at 60° C. After cooling, the pressure vessel was vented, and ethyl acetate was added to dilute the mixture to ~10 to 15% solids. The catalyst was removed by filtration through a 45 μm syringe filter.

Hydrogenation Employing Homogeneous Catalysis

A 200 g sample of a 25% solution of the copolymer of Example 1 was poured into a 2000 ml Parr Pressure Reactor, and 10 ml of a stock solution of Wilkinson's catalyst (0.20 mg/ml in ethyl acetate) was added. The reactor was sealed, then purged twice with 28 bar of nitrogen gas, and twice with 35 bar hydrogen gas. The reaction was pressurized with 44 bar of hydrogen gas and heated to 60° C., which raised the pressure to ~48 bar. The reaction mixture was then stirred at 1000 RPM for 16 hours at 60° C. After cooling, the pressure vessel was vented.

Pressure Filtration

To filter the powdered catalyst from the polymer solutions on a large scale, a Millipore pressure filtration apparatus was used (Millipore #YT30142HW 142 mm Waste Filtration System). Following a hydrogenation experiment, the reactor was not fully vented, nor was the polymer solution allowed to cool. The hydrogen was vented down to 7 bar, and the vessel was repressurized to 21 bar with nitrogen gas; this process was repeated twice more to replace the hydrogen gas with nitrogen gas. The reaction mixture was then vented via the dip tube straight into the filtration apparatus using a pressure of between 7 and 8 bar and a temperature of ~50 to 60° C. A temperature reading taken of the polymer solution exiting from the filtration apparatus showed it to be at ~40° C. The filtration apparatus was kept hot throughout the filtration process by the use of heating tape that was wound around the unit.

What is claimed is:

1. A process for the manufacture of an adhesive comprising one or more olefinic polymers, wherein the content of free monomers is less than 1% by weight, the process comprising, after completion of polymerization or copolymerization of the polymer or polymers, hydrogenation, by reaction with hydrogen gas, of a solution of the adhesive in an organic solvent in the presence of a heterogeneous or homogeneous catalyst.

2. The process according to claim 1, in which the catalyst is the heterogeneous catalyst, palladium on activated carbon.

3. The process according to claim 1, in which the catalyst is the heterogeneous catalyst, nick on silica/alumina.

4. The process according to claim 1, in which the catalyst is the homogeneous catalyst, tris(triphenylphosphine) rhodium (I) chloride.

5. The process according to claim 1, wherein the hydrogenation takes place at temperatures of up to 150° C. and at hydrogen pressures of up to 100 bar.

6. The process according to claim 1, wherein the hydrogenation takes place at temperatures of up to 100° C. and at hydrogen pressures of up to 80 bar.

7. The process according to claim 1, wherein the hydrogenation takes place at temperatures of up to 100° C. and at hydrogen pressures of up to 52 bar.

8. The process according to claim 1, wherein the hydrogenation takes place at room temperature and at atmospheric pressure in the presence of a platinum, palladium, or palladium on carbon (Pd/C) catalyst.

9. The process according to claim 1, wherein the organic solvent is less polar than water.

10. The process according to claim 9, wherein the organic solvent is ethyl acetate.

* * * * *

UNITED STATES PATENT AND TRADEMARK OFFICE
CERTIFICATE OF CORRECTION

PATENT NO. : 5,990,229
DATED : November 23, 1999
INVENTOR(S) : Hille et al.

Page 1 of 1

It is certified that error appears in the above-identified patent and that said Letters Patent is hereby corrected as shown below:

Column 2,
1.52: "wright" should read "weight".

Column 5,
1.44, TABLE 2a: "ppma" should read "ppm$^a$" --(twice).

Column 7,
1.28: "5.μm" should read "5.0 μm".

Column 10,
1.12: "nick" should read "nickel".

Signed and Sealed this

Fourteenth Day of August, 2001

*Attest:*

NICHOLAS P. GODICI
*Attesting Officer*    *Acting Director of the United States Patent and Trademark Office*